US011372006B2

(12) United States Patent
Basey-Fisher et al.

(10) Patent No.: US 11,372,006 B2
(45) Date of Patent: Jun. 28, 2022

(54) METHOD AND APPARATUS FOR DETERMINING HAEMOGLOBIN CONCENTRATION

(71) Applicant: Entia Ltd, London (GB)

(72) Inventors: Toby Basey-Fisher, London (GB); Christopher Burrows, London (GB)

(73) Assignee: Entia Ltd., London (GB)

( * ) Notice: Subject to any disclaimer, the term of this patent is extended or adjusted under 35 U.S.C. 154(b) by 0 days.

(21) Appl. No.: 17/049,885

(22) PCT Filed: Apr. 11, 2019

(86) PCT No.: PCT/GB2019/051051
§ 371 (c)(1),
(2) Date: Oct. 22, 2020

(87) PCT Pub. No.: WO2019/207284
PCT Pub. Date: Oct. 31, 2019

(65) Prior Publication Data
US 2021/0072262 A1 Mar. 11, 2021

(30) Foreign Application Priority Data
Apr. 24, 2018 (GB) .................................. 1806693.6

(51) Int. Cl.
*G01N 33/72* (2006.01)
*G01N 33/49* (2006.01)
(Continued)

(52) U.S. Cl.
CPC ......... *G01N 33/726* (2013.01); *G01N 15/042* (2013.01); *G01N 15/05* (2013.01);
(Continued)

(58) Field of Classification Search
CPC ................. G01N 15/042; G01N 15/05; G01N 2015/0073; G01N 2015/045;
(Continued)

(56) References Cited

U.S. PATENT DOCUMENTS

| 5,898,487 A * | 4/1999 | Hage .................... G01N 21/532 356/39 |
| 2002/0012904 A1* | 1/2002 | Malin .................. G01N 33/721 435/4 |

(Continued)

FOREIGN PATENT DOCUMENTS

| EP | 0795129 B1 | 1/2001 |
| GB | 2525622 A | 11/2015 |

OTHER PUBLICATIONS

International Search Report and Written Opinion for Application No. PCT/GB2019/051051 dated Jun. 28, 2019 (13 pages).

*Primary Examiner* — Maureen Wallenhorst
(74) *Attorney, Agent, or Firm* — Michael Best & Friedrich LLP

(57) ABSTRACT

An apparatus for determining the mean corpuscular haemoglobin concentration (MCHC) in a whole blood sample includes a sample holder including an elongate sample chamber having an open end and a closed end. A holding member is adapted to receive and retain the sample holder. The holding member rotates may rotate about an axis of rotation. When the sample holder is received and retained by the holding member the sample chamber is substantially perpendicular to the axis of rotation. First and second light sources are positioned on one side of the sample holder and are configured to emit light in respective different frequencies. At least one light sensor is positioned on a second side of the sample holder, opposite from the first side, so that light from the light source may pass through the sample
(Continued)

chamber, in at least one rotational position of the sample holder, and impinge on the light sensor.

19 Claims, 3 Drawing Sheets

(51) Int. Cl.
  *G01N 15/04* (2006.01)
  *G01N 15/05* (2006.01)
  *G01N 21/07* (2006.01)
  *G01N 21/31* (2006.01)
  *G01N 15/00* (2006.01)

(52) U.S. Cl.
  CPC ......... *G01N 21/07* (2013.01); *G01N 21/3151* (2013.01); *G01N 33/491* (2013.01); *G01N 33/4925* (2013.01); *G01N 33/721* (2013.01); *G01N 2015/0073* (2013.01); *G01N 2015/047* (2013.01); *G01N 2015/055* (2013.01)

(58) Field of Classification Search
  CPC ....... G01N 2015/047; G01N 2015/055; G01N 21/07; G01N 21/3151; G01N 33/49; G01N 33/491; G01N 33/492; G01N 33/4925; G01N 33/721; G01N 33/726; Y10T 436/25375
  USPC ........ 436/63, 66, 70, 164, 165, 177; 422/72, 422/73, 82.05, 82.09, 533
  See application file for complete search history.

(56) References Cited

U.S. PATENT DOCUMENTS

| | | |
|---|---|---|
| 2005/0051466 A1 | 3/2005 | Carter et al. |
| 2009/0075324 A1* | 3/2009 | Pettersson ............ G01N 21/274 435/39 |
| 2009/0238438 A1* | 9/2009 | Wardlaw ................ G01N 15/05 382/134 |
| 2011/0200239 A1 | 8/2011 | Levine et al. |
| 2014/0273064 A1 | 9/2014 | Smith |

* cited by examiner

METHOD AND APPARATUS FOR DETERMINING HAEMOGLOBIN CONCENTRATION

CROSS-REFERENCE TO RELATED APPLICATION DATA

This application is a U.S. national phase entry of International Application No. PCT/GB2019/051051, filed Apr. 11, 2019, which claims priority to GB Patent Application No. 1806693.6, filed Apr. 24, 2018, the entire contents of which are incorporated herein by reference in their entirety.

BACKGROUND

This invention relates to a method and apparatus for determining some or all of mean corpuscular haemoglobin concentration, haematocrit and haemoglobin concentration in a blood sample.

For many clinical and/or diagnostic purposes it is necessary to determine the concentration of haemoglobin and haematocrit in a blood sample from a subject. However, the measurement of both haemoglobin and haematocrit concentration from a single sample can be difficult without complex equipment or time-consuming techniques. As a result, many point of care instruments measure haemoglobin or haematocrit and calculate the other.

This can be done using the 'rule of three', i.e. 1000×Hct=3×Hb, where Hb represents the haemoglobin concentration and Hct represents the haematocrit. Such a relationship is established based on the assumption that mean corpuscular haemoglobin concentration is fixed for all samples, i.e. MCHC×Hct=Hb. However, the 'rule of three' is an approximation, and may be significantly inaccurate in many clinical cases.

SUMMARY

An object of the invention is to increase the ease with which a reliable determination of haemoglobin and haematocrit can be made, particularly in circumstances where a practitioner will have no access to laboratory equipment, for instance when diagnosing or treating patients in remote locations.

Accordingly, one aspect of the present invention provides Accordingly, one aspect of the present invention provides an apparatus for determining the mean corpuscular haemoglobin concentration (MCHC) in a whole blood sample, comprising: a sample holder including an elongate sample chamber having an open end and a closed end; a holding member adapted to receive and retain the sample holder, wherein the holding member may rotate about an axis of rotation, and wherein, when the sample holder is received and retained by the holding member the sample chamber is substantially perpendicular to the axis of rotation; first and second light sources positioned on one side of the sample holder, configured to emit light in respective different frequencies; and at least one light sensor positioned on a second side of the sample holder, opposite from the first side, so that light from the light source may pass through the sample chamber, in at least one rotational position of the sample holder, and impinge on the at least one light sensor.

Advantageously, light may be emitted from each of the first and second light sources, travel along a path which does not pass through the sample chamber, and impinge upon the at least one light sensor.

Preferably, the holding member has an aperture or window formed therethrough, spaced apart from the sample holder, through which the light may travel.

Conveniently, the light may travel along a path which does not pass through an annular region defined by the rotation of the sample chamber around the axis of rotation, and impinge upon at least one light sensor.

Advantageously, the sample holder is formed at least primarily from a material which is transmissive to the light emitted by the first and second light sources, and wherein the light may travel through a region of the sample holder, spaced apart from the sample chamber thereof, which comprises one or more layers of the material.

Preferably, the at least one light sensor comprises an elongate array of light sensors.

Conveniently, in at least one rotational orientation of the sample holder, the elongate array of light sensors is at least substantially aligned with the sample chamber.

Advantageously, the device comprises at least one further light source, positioned and adapted to emit light which may pass through the sample chamber and be received either by the at least one first light sensor or by one or more alternative light sensors, to determine the length of the sample chamber which is occupied by red blood cells, and the length of the sample chamber which is occupied by other blood components.

Preferably the at least one further light source comprises an elongate array of light sources.

Conveniently, in at least one rotational orientation of the sample holder, the elongate array of light sources is at least substantially aligned with the sample chamber.

Advantageously, the elongate array of light sensors is substantially aligned with the elongate array of light sources.

Preferably, the device comprises an enclosure which is enclosed or substantially enclosed so that ambient light may not enter the interior of the enclosure, and wherein the first and second light sources and the at least one light sensor are positioned within the enclosure.

Conveniently, the device further comprises a motor adapted to drive the holding member about the axis of rotation.

Advantageously, the device further comprises at least one processor which is adapted to receive signals from, and provide instructions to, the first and second light sources and the at least one light sensor.

Preferably, the device further comprises a processor operable to receive output signals from the at least one light sensor, and to calculate the mean corpuscular haemoglobin concentration (MCHC) of the red blood cells of the blood sample from the output signals.

Conveniently, the processor is operable to calculate the haematocrit of the blood sample from the output signals.

Advantageously, the processor is operable to calculate the haemoglobin concentration of the blood sample from the MCHC and the haematocrit thereof.

Preferably, the device further comprises an output device which is operable to output the MCHC, the haematocrit or the haemoglobin concentration of the blood sample.

Conveniently, the output device comprises a screen.

Another aspect of the present invention provides a method of determining the mean corpuscular haemoglobin concentration (MCHC) of a blood sample, comprising the steps of: providing a sample holder; introducing a blood sample into the sample holder; mounting the sample holder on a holding member; rotating the holding member about an axis of rotation, such that the sample chamber is arranged substantially perpendicular to the axis of rotation; providing at least one first light source on a first side of the sample chamber; providing at least one first light sensor on a second side of the sample chamber, opposite from the first side; emitting light from at least one first light source such that the light passes through the sample chamber and is detected by the at least one first light sensor; determining the attenuation of light passing through the sample chamber, and thereby determining the mean corpuscular haemoglobin concentration (MCHC) of the red blood cells of the blood sample.

Advantageously, the method further comprises the step of multiplying the determined MCHC by the haematocrit of the blood sample to determine the total haemoglobin concentration of the blood sample, wherein the haematocrit comprises the ratio of the volume of the red blood cells of the blood sample, during centrifugation, to the total volume of the blood sample.

Preferably, the method further comprises the step of measuring the haematocrit of the blood sample while the blood sample is mounted on the holding member.

Conveniently, the steps of the method are carried out using a device which comprises the holding member, the first light source and the first light sensor, and wherein the device further comprises a processor which is operable to calculate the MCHC, the haematocrit and/or the haemoglobin concentration of the blood sample from output signals received from the first light sensor.

Advantageously, the device further comprises an output device which is configured to output the calculated MCHC, haematocrit and/or haemoglobin concentration of the blood sample.

Preferably the output device comprises a screen.

Conveniently, the step of emitting light from at least one first light source such that the light passes through the sample chamber and is detected by the at least one first light sensor is carried out while holding member is rotated about the axis of rotation.

BRIEF DESCRIPTION OF THE DRAWINGS

In order that the invention may be more readily understood, embodiments thereof will now be described, by way of example, with reference to the accompanying drawings, in which.

DETAILED DESCRIPTION

In embodiments of the invention, a direct measurement is made of the Mean Corpuscular Haemoglobin Concentration (MCHC). For a blood sample, the MCHC is a measure of the concentration of haemoglobin in the red blood cells themselves. MCHC is not, in prior art methods, measured directly, but rather is derived from measurements of the haemoglobin concentration and the haematocrit (which will have been directly measured through other techniques) according to the following formula:

$$MCHC = \frac{Hb}{Hct}$$

In order to measure the MCHC directly, in embodiments of the invention a blood sample is first centrifuged, so that the red blood cells are separated from the other components of the blood sample. As the skilled reader will be aware, a convenient way to achieve this is to collect a sample of blood using a cuvette which includes a sample chamber. The cuvette can then be loaded into a centrifuge, so that the longitudinal axis of the sample chamber is aligned with the axis of rotation around which the cuvette will rotate. The cuvette is then centrifuged, and the red blood cells (being significantly more dense than other components of the blood) will collect and be compacted together at the end of the sample chamber that is furthest from the axis of rotation.

Figures 1A, 1B:
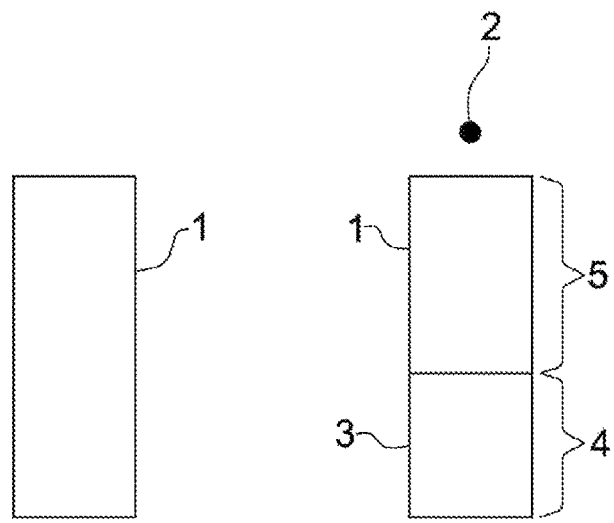
FIGS. 1a and 1b schematically show a blood sample before and after centrifugation, respectively.

FIGS. 1a and 1b are schematic representations of a blood sample within a sample chamber 1, which is shown to be generally elongate and rectangular. In preferred embodiments of the invention the sample that is analysed is a whole blood sample, but this is not essential. In FIG. 1a, the blood sample has not yet been centrifuged, and the components of the blood, including the red blood cells, are generally evenly distributed throughout the sample.

Following centrifugation around an axis of rotation 2, the blood sample has separated into two distinct phases, comprising the red blood cells 3, which are compacted into a volume 4 of the sample chamber 1 which is furthest from the axis of rotation, and the remaining components of the blood sample (i.e. the plasma) in a second volume 5, which is closer to the axis of rotation 2.

A modified Beer-Lambert Law is then used in the determination of the MCHC of the blood sample. By way of background, the modified Beer-Lambert law relates the attenuation of light to the properties of a material. In this case we use the form that relates attenuation of light to the concentration of a substance. It should be noted that there are some assumptions about the substance being inspected in order for the modified Beer-Lambert law to apply. It should also be noted that the modified Beer-Lambert law is used here to account for scattering which is not considered in the Beer-Lambert law. For a single substance this relationship is written as:

$$A = \in \cdot c \cdot l \cdot D + G$$

Where A is the Absorbance, $\in$ is the molar extinction coefficient, C is the concentration of the substance, l is the length of the light path, D is the differential path factor and G is an independent scattering and absorption coefficient. Absorbance can be rewritten in terms of light intensity as follows:

$$A = \log \frac{I_0}{I}$$

Where $I_0$ is the reference intensity value (normally the intensity of the light that is transmitted through the setup with no sample present) and l is the intensity of the light that is actually transmitted through the set up when the sample is present. If there is more than one optically active material (N materials) in the sample then this translates into the generic equation:

$$A_T = \sum_{i=1}^{N} \in_i \cdot C_i \cdot l \cdot D + G$$

Therefore, the total absorption at a certain wavelength is related to all the substances present along the light path.

Figure 2:
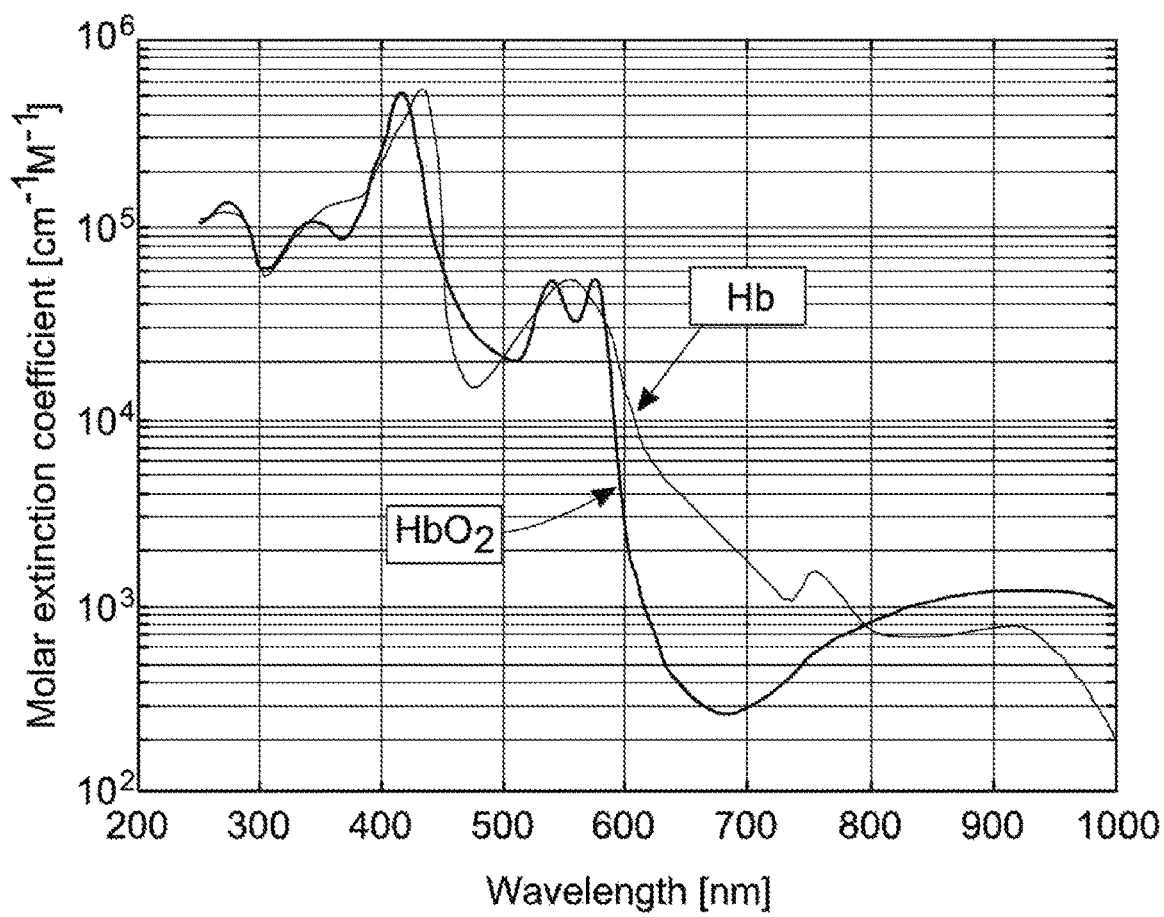
FIG. 2 shows a graph of absorption of different wavelengths of light by the two main species of haemoglobin.

There are two main species of haemoglobin within blood, namely oxygenated haemoglobin ($HbO_2$), which carries at least some oxygen, and reduced haemoglobin (RHb) which does not carry any oxygen. Together these two species make up all, or very nearly all, of the total haemoglobin in a blood sample. These two species have different absorption spectra, which are shown in FIG. 2.

In order to determine the concentration of haemoglobin in the blood sample, the absorption of one or more selected wavelengths of light as the light passes through the sample can be measured. In order to determine separately the concentrations of RHb and $HbO_2$, wavelengths are selected which correspond to portions of the spectrum in which absorption of that wavelength is significantly different between RHb and $HbO_2$. With reference to FIG. 2, it can be seen that 660 nm (red) and 940 nm (near IR) correspond to regions of the spectrum in which the absorption of RHb and $HbO_2$ vary significantly. Moreover, in these regions the spectral lines are relatively 'flat' (i.e. relatively invariant with respect to small changes in wavelength), and for both reasons these regions of the spectrum are effective in providing measurements that allow the determination of light absorption by both RHb and $HbO_2$ species.

The skilled reader will appreciate that this is similar in certain respects to the technique used in pulse oximetry (co-oximetry), which involves measuring the light transmitted through part of a person's body, for instance the person's fingertip. The use of the two different wavelengths, as discussed above, allows differentiation between the two main haemoglobin species in blood.

The total concentration of haemoglobin may be expressed as:

[Hb]=[HbO2]+[RHb]

In terms of the Beer-Lambert law this translates to the following:

$$A_1 = \epsilon_{O_1} \cdot C_O \cdot l_1 \cdot D_1 + \epsilon_{R_1} \cdot c_R \cdot l_1 \cdot D_1 + G$$

$$A_2 = \epsilon_{O_1} \cdot C_O \cdot l_2 \cdot D_2 + \epsilon_{R_1} \cdot c_R \cdot l_2 \cdot D_2 + G$$

Where O and R subscripts denote the constants associated with $HbO_2$ and RHb respectively and $_1$ and $_2$ are the two wavelengths. Solving for $C_o$ and $C_R$ respectively gives the following:

$$c_O = \frac{\epsilon_{R_2} \cdot l_2 \cdot D_2 (G - A_1) + \epsilon_{R_1} \cdot l_1 \cdot D_1 (A_2 - G)}{(\epsilon_{R_1} \cdot \epsilon_{O_2} - \epsilon_{O_1} \cdot \epsilon_{R_2}) \cdot l_1 \cdot D_1 \cdot l_2 \cdot D_2}$$

$$C_R = \frac{\epsilon_{O_2} \cdot l_2 \cdot D_2 (A_1 - G) + \epsilon_{O_1} \cdot l_1 \cdot D_1 (G - A_2)}{(\epsilon_{R_1} \cdot \epsilon_{O_2} - \epsilon_{O_1} \cdot \epsilon_{R_2}) \cdot l_1 \cdot D_1 \cdot l_2 \cdot D_2}$$

Therefore, in order for the method to be effective the constants $\epsilon_{O_1}$, $\epsilon_{O_2}$, $\epsilon_{R_1}$ and $\epsilon_{R_2}$ need to be determined accurately. For single or narrow bandwidth light sources this is relatively easy as the absorption curves of FIG. 2 can be used. However, in practice broadband LEDs need to be used in order to keep the cost and space requirements of the device down. The constants $l_1$, $l_2$, $D_1$, $D_2$ and G also need to be determined but are generally properties of the setup.

To determine these constants for LED light sources, assuming that the broad spectrum can be averaged to one extinction coefficient, an empirical study has to be done. This is normally done through multivariate analysis, and the skilled reader will readily understand how this may be achieved.

Figure 3:
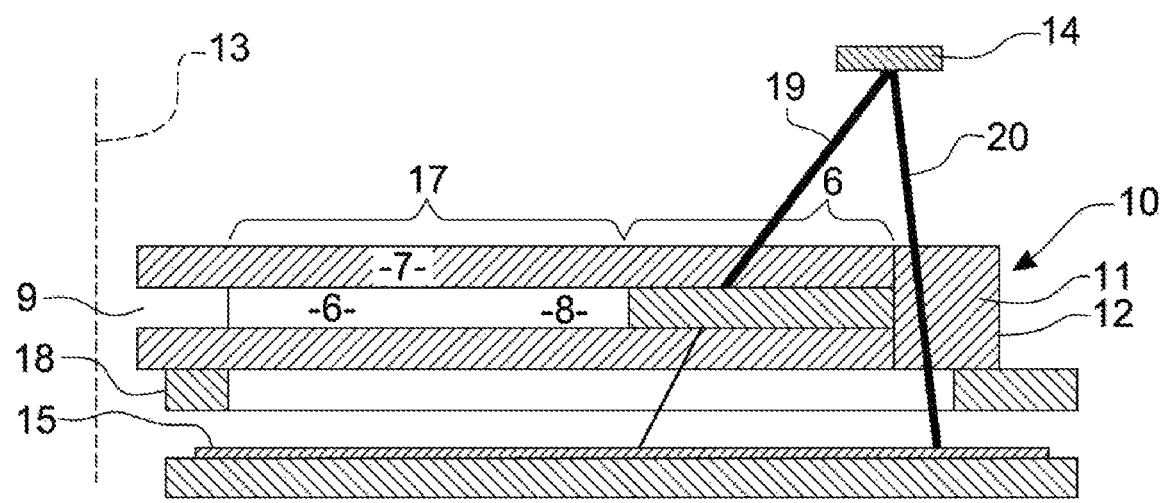
FIGS. 3 and 4 show parts of a device embodying the present invention.
Figure 4:
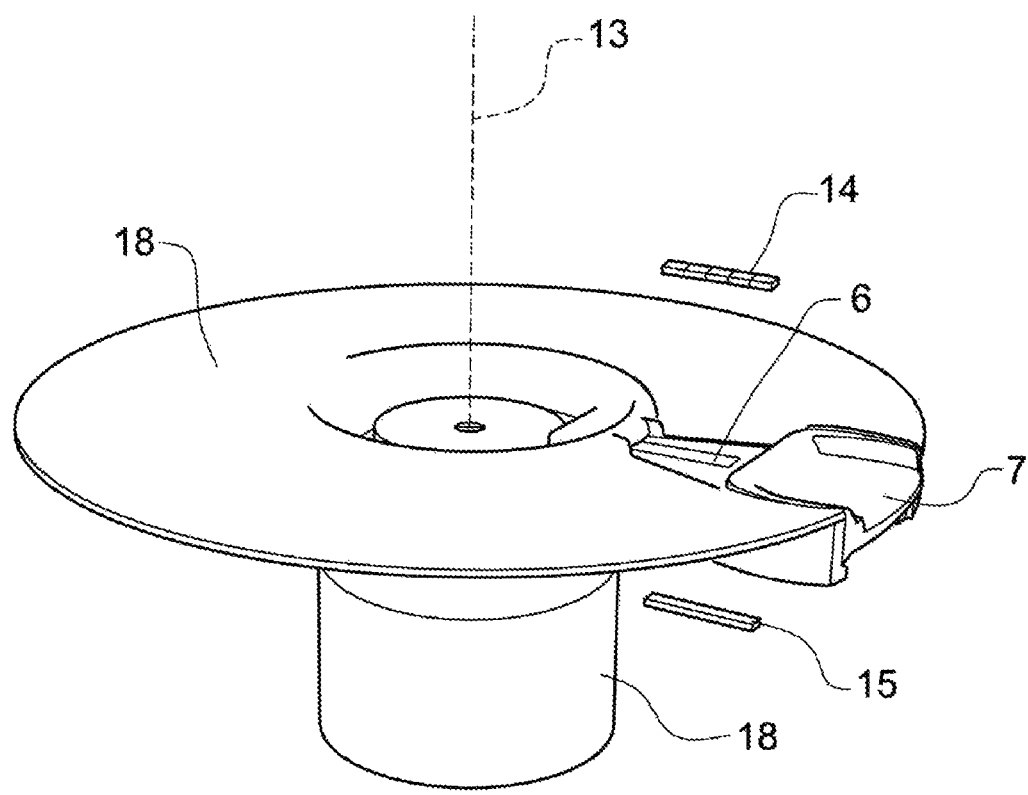

FIGS. 3 and 4 show features of equipment suitable for carrying out the invention. As discussed above, a blood sample 6 is loaded into a cuvette 7, which includes an elongate sample chamber 8. The sample chamber 8 has an open end 9, into which the blood sample is initially introduced, and a closed end 10. In the example shown, the sample chamber 8 has a generally rectangular cross-sectional shape along its length, although other cross-sectional shapes are possible (although, as will be clear from the discussion below, it is preferred that the cross-sectional size and shape of the sample chamber 8 remains the same along all, or substantially all, of its length). Adjacent the closed end 10 is a reference region 11 of the cuvette, which comprises a region in which the entire depth of the cuvette 7 is formed from a single, integral quantity of relatively transmissive material. In preferred embodiments, the cuvette is formed from a relatively transmissive glass or plastic material, and the reference region 11 of the cuvette 7 comprises an integral, unbroken region of this material occupying the entire depth of the cuvette 7 at this point.

In the embodiment shown in FIG. 3, the cuvette has a length which passes from the open end 9 towards the closed end 10 of the sample chamber 8, and extends beyond the closed end 10 of the sample chamber 8 to reach a second end 12 of the cuvette 7 itself. The reference region 11 of the cuvette 7 in this example comprises a solid, integral region of the material from which the cuvette 7 is formed, extending at least some of the way between the closed end 10 of the sample chamber and the second end 12 of the cuvette 7 itself.

In preferred embodiments, the cuvette is loaded into a sample holder 18, which is adapted to receive and retain the cuvette 7 in a stable fashion while the cuvette 7 undergoes centrifugation. The sample holder 18 may take the form of a generally disc-shaped component having a central aperture which is adapted to be mounted onto a central drive shaft of the centrifuge. The sample holder 18 includes an aperture 19, which is at least aligned with the sample chamber 8 so that, in the region of the sample chamber 8, the sample holder 18 does not present any optical obstruction to light passing through the sample chamber 8 in a direction which is generally parallel with the axis of rotation 13.

In some embodiments, the aperture 19 may be of approximately the same size and shape as the cuvette 7 itself, so that the entire cuvette 7 may be mounted in the aperture 19.

In embodiments of the invention, a reference region is provided in the sample holder 18, rather than the cuvette 7, and may for instance comprise a window or aperture passing through the depth of the sample holder 18 at a position which is radially spaced from the location at which the cuvette 7 is held.

Once the blood sample 8 has been introduced into the sample chamber 6 of the cuvette 7, the cuvette 7 is loaded into a centrifuge (preferably, as discussed above, by being mounted in a sample holder 18 of the centrifuge). The centrifuge has an axis of rotation 13, and the cuvette 7 is introduced so the sample chamber 6 is arranged with its length generally perpendicular to the axis of rotation 13. The open end 9 of the sample chamber 6 lies closest to the axis of rotation 13, with the closed end 10 of the sample chamber 6 being furthest from the axis of rotation 13.

Two light sources are positioned on one side of the cuvette 7 (in the orientation shown in FIG. 3, the light sources 14 are positioned above the cuvette 7). In this embodiment, one of the light sources 14 is configured to emit radiation at or in the region of 660 nm, and the other of the light sources 14 is configured to emit radiation at or in the region of 940 nm.

The two light sources 14 are preferably provided close together. In preferred embodiments the two light sources 14 are provided at the same, or substantially the same, position with respect to the length of the sample chamber, i.e. side by side.

Arranged on the other side of the cuvette 7 (in the orientation shown in FIG. 3, below the cuvette 7) one or more light sensors are provided. The light sensors are configured to detect light emitted by the light sources 14.

In the embodiment shown in FIG. 3, a linear light sensor 15 is provided, being positioned generally opposite the light sources 14 and arranged so that the longitudinal axis of the linear light sensor 15 extends generally away from the axis of rotation. The linear light sensor 15 has a number of individual light sensors arranged along the axis, and may for example comprise an elongate CCD.

The overall arrangement of components is that, at at least one point in the rotation of the cuvette 7 around the axis of the rotation 13 of the centrifuge, light 19 from each of the light sources 14 may be emitted, pass through the sample chamber 8 of the cuvette 7, and be received by at least one part of the linear light sensor 15.

Also, at at least one point in the rotation of the cuvette 7, the components are arranged so that light 20 may be emitted by each of the light sources 14, pass through the reference region 11 of the cuvette 7, and be received by a region of the light sensor 15. In other embodiments, the light emitted by each of the light sources may pass through a reference region in a different part of the sample holder 18.

In a method embodying the invention, the cuvette 7 is rotated around the axis of rotation 13 until the red cells of the blood sample are compacted in a stable manner into a first region 16 of the sample chamber 8, which is closest to the closed end 10 thereof. The remaining components of the blood (i.e. the plasma) accumulate in a second region 17 of the sample chamber 8, closest to the open end 9 thereof.

When the sample chamber 8 is aligned between the light sources 14 and the light sensor 15, light from each of the light sources 14 is emitted in a direction such that it will pass through the first region 16 of the sample chamber 8, and then impinge on the light sensor 15. Signals from the light sensor 15 will allow the determination of the intensity of the light from the light sources 14 that has reached the light sensor 15.

In preferred embodiments, the light sources 14 are illuminated sequentially so that, in any particular rotation of the cuvette 7, light from only one light source is emitted. This allows each reading received by the light sensor 15 to be determined as corresponding to light of a particular known wavelength that has been transmitted through the cuvette 7.

In addition, during at least one rotation of the cuvette 7, light from each of the light sources is emitted, passes through the reference region 11 of the cuvette 7, and impinges on the light sensor 15. In other embodiments, during at least one rotation of the cuvette 7, light from each of the light sources is emitted, passes through a reference region in a different part of the sample holder 18, and impinges on the light sensor 15.

In embodiments of the invention, the light from the light sources 14 is not "directed", and is emitted in at least a first direction which passes through the first region 16 of the sample chamber 8, and then impinges on the light sensor 15, and in a second direction which passes through the reference region 11 of the cuvette 7, and impinges on the light sensor 15.

However, in other embodiments, the light from the light sources 14 may be directed so that, in a first configuration, each light source 14 emits illumination in a first direction, passing through the first region 16 of the sample chamber 8 and then impinging on the light sensor 15, and in a separate, second direction which passes through the referenced region 11 of the cuvette 7 and then impinges on the light sensor 15.

In other embodiments of the invention, the light from the light sources 14 is not "directed", and is emitted in at least a first direction which passes through the first region 16 of the sample chamber 6, and then impinges on the light sensor 15, and in a second direction which passes through a reference region in a different location on the sample holder 18, and impinges on the light sensor 15.

As the skilled reader will appreciate, the measured intensity of the light from the light sources 14 that arrives at the light sensor 15 through the reference region 11 of the cuvette 7 represents the reference intensity value $I_0$ of the light. This can be used, along with the measured intensity of the light that has passed through the red blood cells of the sample, to determine the absorbance for a particular wavelength of light, according to the equation given above.

In other embodiments, the skilled reader will appreciate that the measured intensity of light from the light sources 14 that arrives at the light sensor 15 through a reference region in a different location on the sample holder 18 can represent the reference intensity value $I_0$ of the light. This can be used, along with the measured intensity of the light that has passed through the red blood cells of the sample, to determine the absorbance for a particular wavelength of light, according to the equation given above.

In prior art methods, in order to determine total haemoglobin concentration in a sample, typically the red blood cells have to be evenly distributed throughout the sample. The light attenuation through the sample or part of the sample is then used to determine the total haemoglobin concentration. However, using the method described above, all of the red blood cells are compacted into one location, which comprises a packed cell volume. Therefore, the local haemoglobin concentration is increased due to all of the haemoglobin within the sample being contained within the packed cell volume. Because only the red cells are contained within the packed cell volume, the measured haemoglobin concentration from this volume is the mean corpuscular haemoglobin concentration (MCHC) of the sample. Therefore, light attenuation in the packed cell volume is linearly related to MCHC.

By comparing the degree to which light passing through the first region 16 of the cuvette 7 is attenuated, with the attenuation of light passing through the reference region 11 of the cuvette 7, a direct measurement of MCHC can be made.

In preferred embodiments of the invention, a measurement of the haematocrit of the sample is also made. In aspects of the invention, a measurement of the haematocrit of the sample is made while the blood sample is within the same device that is used to measure the attenuation of light passing through the sample. In yet further preferred embodiments, the measurement of the MCHC can be made, as discussed above, and a measurement of the haematocrit of the sample can be made, without removing the cuvette (or other device that holds the blood sample) from the centrifuge. The two measurements may even be made during the same session of centrifugation, i.e. the sample can be centrifuged, and the two measurements made while the sample is rotating, without bringing the cuvette to a halt between the two measurements.

As the skilled reader will appreciate, measurement of the haematocrit could be done by providing an elongate array of light sources on one side of the cuvette, extending along substantially the entirety of the length of the sample chamber 8, or at least all of the length of the sample chamber 8 in which the blood sample 8 will be contained. A linear array of light sensors may be positioned on the opposite side of the cuvette 7 from the array of light sources. Light from the light sources may pass through the sample chamber 8 and be received by the linear array of light sensors. From the information received from the linear array of light sensors, the length of the first portion 16 of the blood sample 8 may be derived, along with the length of the second portion 17 of the blood sample 8. As the skilled reader will understand, the red blood cells will be least transmissive to radiation, followed by the other components of the blood. The other regions of the cuvette (i.e. which do not contain any part of the blood sample) will be more transmissive still. From the relative intensity of light impinging on the linear array of light sensors, the lengths of the first and second portions 16, 17 of the blood sample 8 may be calculated.

As an alternative to the above, measurement of the haematocrit of the sample may be carried out using one or both of the same light sources 14 that are used in the measurement of attenuation of light by the red blood cells in the sample, although it is preferred that a separate array of light sources is used to measure the haematocrit.

In embodiments of the invention, a linear array of light sources is used in the measurement of the haematocrit, and the two light sources 14 that are used in the measurement of attenuation of light by the red blood cells in the sample are positioned on either side of this linear array.

The ratio between (a) the first length, and (b) the total of the two lengths may then be calculated, to give the haematocrit, which (as mentioned above) is defined as the ratio of the volume of the red blood cells to the total volume of the blood sample.

Once the MCHC and the haematocrit of the sample have been measured, the total haemoglobin concentration can be determined, using the formula:

$$Hb = Hct \times MCHC$$

The skilled reader will appreciate that the above represents a straightforward apparatus and method for determining the haemoglobin and haematocrit of a blood sample, which can be carried out using a relatively compact apparatus and at relatively low cost.

In the discussion above, two light sources which emit light at different frequencies are used to determine the concentration of the two major haemoglobin species in blood. In practice, almost any two frequencies may be used, and the invention is not limited to the frequencies discussed above. Alternatively, one light source could be used, which preferably emits light in a wavelength at which the transmissivity of the two species is the same, or substantially the same (this is known as an isosbestic point). Returning to FIG. 2, 800 nm is an example of a suitable isosbestic point for analysis of haemoglobin species in blood.

Effective measurement of attenuation at the isosbestic point is likely to require a laser or a narrow-band filtered light source which is carefully tuned to the correct frequency. At the time of writing, inclusion of a laser of this kind is likely to be prohibitively expensive, increase the size of the device, and also require compliance with relatively stringent safety measures. While this is not ruled out as a possibility, it is currently preferred to use LEDs as the light sources.

In the discussion above, light is shown to be emitted from the light sources 14 in a direction that passes through the red blood cells of the blood sample, and impinges on the light sensor 15. In preferred embodiments, however, several different readings of the transmissivity of the red blood cells are taken. This may be achieved by measuring the intensity of light received by the light source 15 along a number of different, spaced-apart paths, each of which passes through the red blood cells and impinges on the light sensor. In other words, a first light path may pass through the red blood cells relatively close to the closed end of the sample chamber, a second light path may pass through the red blood cells at a greater distance from the closed end of the sample chamber and so on.

With reference to FIG. 3, it can be seen that in any particular set-up, the angle at which the radiation will pass through the blood cells will change from one path to the next, and therefore the path length of the radiation through the red blood cells will also change. When considering the intensity of light received at the light sensor along the various light paths, this can be compensated for by use of geometry to consider the correct length of path through the red blood cells that the light has travelled. The same is true of the light path through a reference region.

As discussed above, the illumination from each light source 14 may be emitted in a generally uniform fashion over the length of the sample chamber, in this case, the intensity of light received by the light sensor 15 at several different locations may be measured, with each measurement corresponding to light which has travelled along a different path through the red blood cells of the sample. In other embodiments, if light from the light sources 14 may be directed, the light may be directed along a number of different paths, with the intensity of light received at the light sensor 15 being measured in each case.

The sample holder may include one or more calibration or timing features, which will allow determination of the rotational position of the sample holder within the device. For instance, the sample holder may have (radially spaced apart from the position of the cuvette) a series of apertures of known size, spacing and position. As the sample holder rotates one of the light sources of the device may be illuminated, and the light sensors will receive a number of "flashes" as the calibration/timing features are respectively aligned between the light source and the light sensor. Use of features such as this to coordinate the operation of the device is known and will not be discussed in detail here.

In practice, a device embodying the present invention may comprise a selectively openable/closable enclosure having an interior, wherein all or substantially all ambient light is blocked from the interior when the enclosure is in the closed position. The enclosure may, for example, generally take the form of a box having a lid.

Within the enclosure is a drive shaft, onto which the sample holder may be fitted, and which may be driven to rotate at a suitable rate for centrifugation. A motor of a suitable kind is provided to drive the drive shaft, and is preferably compactly positioned within the device.

Figure 5:
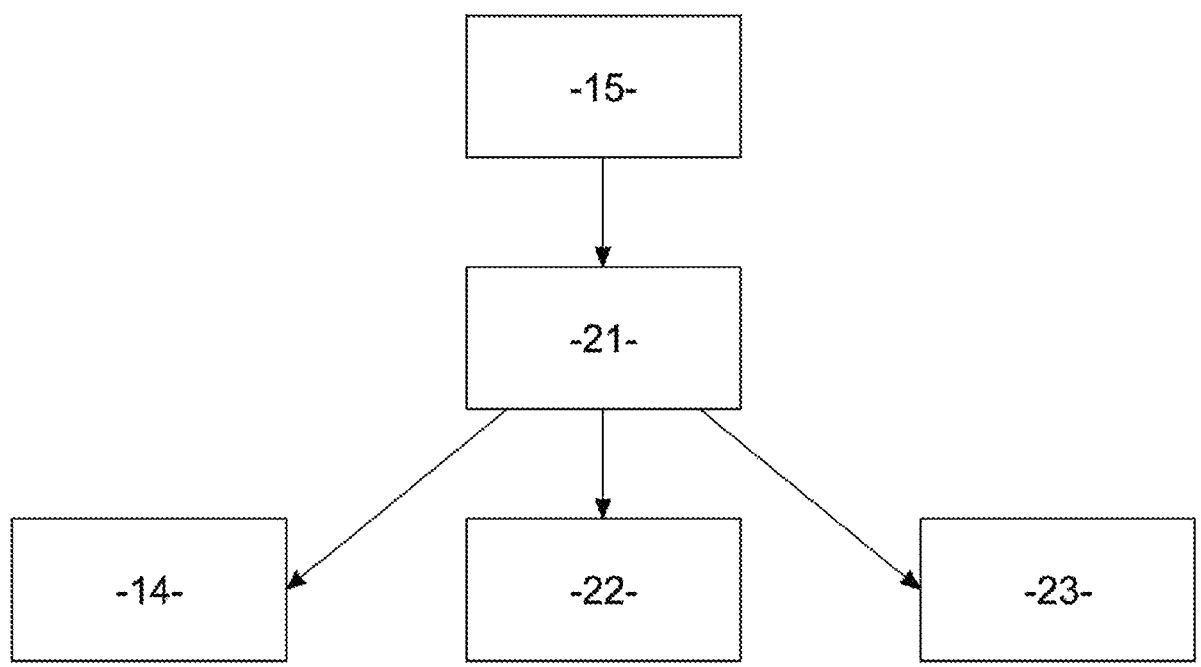
FIG. 5 is a schematic view of parts of a device embodying the present invention.

The device preferably also comprises one or more processors 21, which are adapted (as shown in FIG. 5) to provide instructions to the motor 22, and the various light sources 14 of the device, and to receive signals from the various light sensors 15. The processor may also be able to manipulate data gathered from the light sensors 15 to produce values for one or more of the MCHC, the haematocrit, and the haemoglobin concentration. The device may comprise a screen 23 on which some or all of these values may be displayed.

Alternatively, or in addition, the device may comprise a data output, which may allow data gathered by the device to be transmitted to a further computing device. In some embodiments, the "raw" data gathered by the device will be transmitted to one or more further computing devices, which will then calculate the MCHC, the haematocrit, and/or the haemoglobin concentration from this raw data.

The device preferably also comprises a first memory, on which instructions are stored for the operation of the components of the device, and a second memory, on which data gathered by the device may be stored. The first and second memories may comprise different regions/portions of the same memory, which may take any suitable form.

The device preferably also comprises a power source, which provides power to drive the components of the device. The power source may comprise one or more batteries (which may be rechargeable batteries), and/or a connection to an external power supply, such as a mains power supply. It is envisaged that the device will find particular utility in remote locations, where a mains power supply or the like may not be readily available, and it is therefore preferred that the device can be operated using batteries.

The invention relates to analysis of a blood sample that has been taken from a patient. It is not intended that the blood is returned to the patient, and preferably the blood sample is destroyed or discarded following analysis. The analysis is performed in vitro (i.e. ex vivo) and the sample is isolated from the patient.

It will be appreciated that the present invention provides simple, robust and reliable methods for determining the haemoglobin and haematocrit of a blood sample. As the reader will appreciate, in embodiments of the invention a blood sample may be gathered using a cuvette, and loaded into a compact and convenient device (which may be small enough to be easily handheld and portable). The device then analyses the sample swiftly, and provides, on a screen of the device itself, a reliable direct measurement of the haemoglobin, haematocrit and/or MCHC concentration of the sample. As those skilled in the art will realise, this is a simple solution for the determination of haemoglobin and haematocrit compared to existing methods.

When used in this specification and the claims, the term "comprises" and "comprising" and variations thereof mean that specified features, steps or integers and included. The terms are not to be interpreted to exclude the presence of other features, steps or compounds.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realising the invention in diverse forms thereof.

The invention claimed is:

1. An apparatus for determining a mean corpuscular haemoglobin concentration (MCHC) in a whole blood sample, comprising:
   a sample holder including an elongate sample chamber having an open end and a closed end;
   a holding member adapted to receive and retain the sample holder, wherein the holding member is configured to rotate about an axis of rotation, and wherein, when the sample holder is received and retained by the holding member the sample chamber is substantially perpendicular to the axis of rotation;
   first and second light sources positioned on a first side of the sample holder, configured to emit light in respective different frequencies, which correspond to regions of the spectrum in which absorption of reduced haemoglobin (RHb) and oxygenated haemoglobin (HbO$_2$) vary significantly;
   at least one light sensor positioned on a second side of the sample holder, opposite from the first side, so that light from each of the first and second light sources passes through the sample chamber, in at least one rotational position of the sample holder, and impinges on the at least one light sensor, to allow determination of light absorption by both RHb and HbO$_2$ species; and (a) a processor configured to receive output signals from the at least one light sensor, and to calculate the mean corpuscular haemoglobin concentration (MCHC) of the red blood cells of the blood sample from the output signals, wherein the output signals are representative of the light absorption by both the RHb and HbO$_2$ species, and/or (b) a data output to transmit data gathered by the apparatus to a further computing device, wherein the further computing device is configured to calculate the MCHC from the output signals.

2. The apparatus according to claim 1, wherein light is emitted from each of the first and second light sources, travels along a path which does not pass through the sample chamber, and impinges upon the at least one light sensor.

3. The apparatus according to claim 2, wherein the holding member has an aperture or window formed therethrough, spaced apart from the sample holder, through which the light travels.

4. The apparatus according to claim 2, wherein the light travels along a path which does not pass through an annular region defined by the rotation of the sample chamber around the axis of rotation, and impinges upon the at least one light sensor.

5. The apparatus according to claim 4, wherein the sample holder is formed at least primarily from a material which is transmissive to the light emitted by the first and second light sources, and wherein the light travels through a region of the sample holder, spaced apart from the sample chamber thereof, which comprises one or more layers of the material.

6. The apparatus according to claim 1, wherein the at least one light sensor comprises an elongate array of light sensors.

7. The apparatus according to claim 1, comprising at least one further light source, positioned and adapted to emit light which passes through the sample chamber and is received either by the at least one light sensor or by one or more alternative light sensors, to determine a length of the sample chamber which is occupied by red blood cells, and a length of the sample chamber which is occupied by other blood components.

8. The apparatus according to claim 7, wherein the at least one further light source comprises an elongate array of light sources.

9. The apparatus according to claim 8 wherein, in at least one rotational orientation of the sample holder, the elongate array of light sources is at least substantially aligned with the sample chamber.

10. The apparatus according to claim 1, comprising an enclosure which is enclosed or substantially enclosed so that ambient light does not enter an interior of the enclosure, and wherein the first and second light sources and the at least one light sensor are positioned within the enclosure.

11. The apparatus according to claim 1, further comprising a motor adapted to drive the holding member about the axis of rotation.

12. The apparatus according to claim 1, wherein the processor is configured to receive signals from, and provide instructions to, the first and second light sources and the at least one light sensor.

13. The apparatus according to claim 1, wherein the processor is operable to calculate the haematocrit of the blood sample from the output signals.

14. The apparatus according to claim 13, wherein the processor is operable to calculate the haemoglobin concentration of the blood sample from the MCHC and the haematocrit thereof.

15. A method of determining a mean corpuscular haemoglobin concentration (MCHC) of a blood sample, comprising the steps of:
providing a sample holder;
introducing a blood sample into the sample holder;
mounting the sample holder on a holding member;
rotating the holding member about an axis of rotation, such that a sample chamber in the sample holder is arranged substantially perpendicular to the axis of rotation;
providing first and second light sources on a first side of the sample chamber;
providing at least one first light sensor on a second side of the sample chamber, opposite from the first side;
emitting light from the first and second light sources at respective different frequencies, which correspond to regions of the spectrum in which absorption of reduced haemoglobin (RHb) and oxygenated haemoglobin ($HbO_2$) vary significantly, such that the light passes through the sample chamber and is detected by the at least one first light sensor;
determining separately an attenuation of light passing through both RHb and $HbO_2$ species in the sample chamber by measuring the attenuation of the light emitted from the first and second light sources with the at least one first light sensor, and determining the mean corpuscular haemoglobin concentration (MCHC) of the red blood cells of the blood sample using output signals representative of the measured attenuation of light passing through both the RHb and $HbO_2$ species.

16. A method according to claim 15, further comprising the step of multiplying the determined MCHC by the haematocrit of the blood sample to determine the total haemoglobin concentration of the blood sample, wherein the haematocrit comprises a ratio of the volume of the red blood cells of the blood sample, during centrifugation, to a total volume of the blood sample.

17. A method according to claim 16, further comprising the step of measuring the haematocrit of the blood sample while the sample holder containing the blood sample is mounted on the holding member.

18. A method according to claim 15, wherein the steps of the method are carried out using a device which comprises the holding member, the first and second light sources and the at least one first light sensor, and wherein the device further comprises a processor which is operable to calculate the MCHC, the haematocrit and/or the haemoglobin concentration of the blood sample from output signals received from the at least one first light sensor.

19. A method according to claim 18, wherein the step of emitting light from the first and second light sources such that the light passes through the sample chamber and is detected by the at least one first light sensor is carried out while the holding member is rotated about the axis of rotation.

* * * * *